United States Patent [19]

Tennican et al.

[11] Patent Number: 5,417,667
[45] Date of Patent: May 23, 1995

[54] CATHETER ACCESS SYSTEM AND METHOD

[75] Inventors: Patrick O. Tennican; L. Myles Phipps; Russell A. Michaelsen, all of Spokane, Wash.

[73] Assignee: Hyprotek, Inc., Spokane, Wash.

[21] Appl. No.: 228,699

[22] Filed: Apr. 18, 1994

Related U.S. Application Data

[63] Continuation-in-part of Ser. No. 48,906, Apr. 19, 1993, Pat. No. 5,308,322, and a continuation-in-part of Ser. No. 187,632, Jan. 26, 1994.

[51] Int. Cl.⁶ .............................. A61M 5/00
[52] U.S. Cl. ............................... 604/191; 604/248; 128/DIG. 12
[58] Field of Search ............. 604/82, 83, 85, 89, 604/93, 191, 212, 246, 248, 249, 258, 403; 206/828; 222/135, 137; 128/DIG. 12

[56] References Cited

U.S. PATENT DOCUMENTS

| | | | |
|---|---|---|---|
| 869,702 | 10/1907 | Friend . | |
| 1,948,388 | 2/1934 | Liberson | 604/191 |
| 2,254,994 | 9/1941 | Butland | 604/83 |
| 2,680,455 | 6/1954 | Raiteri . | |
| 3,051,174 | 8/1962 | Mandell . | |
| 3,128,920 | 4/1964 | Volckening et al. | 604/212 |
| 3,678,959 | 7/1972 | Liposky | 137/625.11 |
| 3,678,960 | 7/1972 | Leibinsohn | 137/625.47 |
| 3,957,082 | 5/1976 | Fuson et al. | 604/248 |
| 4,109,653 | 8/1978 | Kozam et al. | 128/218 |
| 4,367,737 | 1/1983 | Kozam et al. | 128/215 |
| 4,609,371 | 9/1986 | Pizzino | 604/191 |
| 4,610,666 | 9/1986 | Pizzino | 604/191 |
| 4,666,429 | 5/1987 | Stone | 604/83 |
| 4,758,235 | 7/1988 | Tu | 604/248 |
| 4,784,157 | 11/1988 | Halls et al. | 128/762 |
| 4,795,441 | 1/1989 | Bhatt | 604/124 |
| 4,915,688 | 4/1990 | Bischof et al. | 604/83 |
| 4,950,230 | 8/1990 | Kendell | 604/248 |
| 5,037,390 | 8/1991 | Raines et al. | 604/83 |
| 5,163,554 | 11/1992 | Lampropoulos et al. | 206/363 |
| 5,205,820 | 4/1993 | Kriesel | 604/85 |
| 5,336,188 | 8/1994 | Kriesel | 604/85 |

FOREIGN PATENT DOCUMENTS

| | | |
|---|---|---|
| 737249 | 6/1966 | Canada . |
| 0299562 | 1/1989 | European Pat. Off. ............ 206/828 |
| US91/09718 | 7/1992 | WIPO . |

OTHER PUBLICATIONS

"Three Easy Steps to More Convenient SASH.", product brochure, Block Medical, Inc. (California Jun. 1993).

Primary Examiner—C. Fred Rosenbaum
Assistant Examiner—Frank Wilkens, III
Attorney, Agent, or Firm—Wells, St. John, Roberts, Gregory & Matkin

[57] ABSTRACT

A catheter access system includes upper and lower laminated sheets. The upper sheet is integrally molded to form a plurality of longitudinally-extending syringe channels. The second sheet extends along the syringe channels to enclose them from beneath and to form a plurality of syringe barrels. An independently operable syringe plunger is slidably received within each syringe barrel. A syringe barrel selection valve is formed between the upper and lower sheets. It has a plurality of individually-selectable valve inlets, as well as a single valve outlet for fluid connection to a catheter access line in a patient. The laminated upper and lower sheets define individual fluid passages connecting individual syringe barrels to corresponding individual valve inlets. The syringe barrel selection valve can be turned to provide fluid communication between the valve outlet and any one of the syringe barrels.

24 Claims, 4 Drawing Sheets

CATHETER ACCESS SYSTEM AND METHOD

RELATED PATENT DATA

This patent resulted from a continuation-in-part patent application of U.S. patent application Ser. No. 08/187,632, filed Jan. 26, 1994 entitled "Catheter Access System and Method," now U.S Pat. No. 5,411,485; and U.S. patent application Ser. No. 08/048,906, filed Apr. 19, 1993 entitled "Central Venous Catheter Access System And Syringes," now U.S. Pat. No. 5,308,322.

TECHNICAL FIELD

This invention relates to methods of and systems for accessing catheters which are invasively inserted relative to a patient's blood stream, and to the maintenance of such catheters.

BACKGROUND OF THE INVENTION

Catheters are commonly used to provide quick and direct access to a patient's blood stream. Commonly used catheters range from intravenous lines, which are used in a variety of routine situations, to central venous catheters (CVC), which are used in critical care situations. Catheter maintenance can be costly and troublesome, especially for all but the simplest short-term catheters such as those which access a patient's arm vein.

For example, a CVC is inserted by a surgical procedure in a vein very near the heart. A CVC is often left in place for a relatively long time. The skin entry point is kept covered by a carefully monitored dressing. Because of the direct nature of access to the blood stream, infection control when dealing With CVCs is of utmost importance. In most institutions, only registered nurses and doctors are allowed to perform procedures relating to CVC access.

A CVC includes one or more external access lumens, each having a terminus injection/withdrawal port which typically includes a needle-less connector such as a Luer-lok connector. To allow injection or withdrawal of fluids through the CVC, the connector is typically connected to a mating piece having a pierceable rubber membrane. Fluid transfer requires first cleaning the pierceable membrane with alcohol and/or Betadine, and then inserting a hypodermic syringe needle through the membrane to provide direct access to the blood stream. In some cases, syringes are connected directly to the CVC's connector without a needle, thereby eliminating the need for the pierceable membrane.

CVC access lumens can become clogged by clotted blood and fibrin. The access lumens are kept free from clots when not in use by injecting a heparin solution into them. This is commonly referred to as a heparin lock. Heparin is a protein material which acts as a blood anticoagulant. Before withdrawing a blood sample from a CVC, the heparin and the blood-containing heparin in the catheter is first withdrawn. Also, depending on the patient's condition and the type of catheter, it is sometimes desirable or necessary to withdraw heparin from the catheter before injecting a medication through the catheter.

There are significant risks associated with transferring fluid through a CVC. One risk is that of microbial infection. Another significant risk is that of air embolism. Both of these risks are potentially life-threatening and increase significantly with each access through the CVC access lumen, especially when such an access is by way of a needle and pierceable membrane. Compounding these risks is the fact that a single medication injection procedure or a single blood collection procedure can require four or more separate connections to the CVC access lumen, one for each separate fluid injection and withdrawal. In some cases, the CVC is used for medication injection or blood withdrawal as many as four to six times each day. Thus, as many as twenty-four CVC connections are required every day, with a corresponding number of opportunities for infection or air embolism. Over the period of a month, the CVC could present over 700 opportunities for life-threatening events to occur.

As an example, a simple medication injection procedure requiring heparin withdrawal includes the following steps. First, the pierceable membrane of the injection port must be cleaned with alcohol. The success of this step is highly dependent on the skill of the care-giver and is subject to mistakes caused by carelessness or inattentiveness. A needle of a waste blood withdrawal syringe is then inserted through the membrane. The syringe is operated to withdraw the heparin-containing blood from the CVC. Next, the catheter is flushed with a saline syringe. A medication syringe is then prepared, its needle inserted through the pierceable membrane, and medication injected into the CVC. Subsequently, another saline flush syringe is prepared and its contents injected to carry all the medication into the patient's blood stream. Finally, heparin is injected into the CVC through the pierceable membrane to re-establish the heparin lock. If all this is done quickly and correctly, the catheter will not clot, no air embolism will result, and the patient will not be infected.

Withdrawing or collecting blood requires similar steps. First, all heparin-containing blood is withdrawn from the CVC transfer lumen by injecting a needle through the pierceable membrane and withdrawing blood into a waste blood withdrawal syringe. After the heparin-containing blood is completely withdrawn from the catheter, the waste withdrawal needle is removed and a needle of another syringe is inserted to withdraw non-heparin contaminated blood. Then a normal saline flush is injected, followed by a heparin injection with yet another needle and syringe to establish a heparin lock.

As is apparent from the above discussion, another problem with standard CVC access procedures is that the various solutions and syringes needed to access a CVC are supplied separately. A nurse must often collect these materials from different places. This can be a costly and time consuming process. Furthermore, even after proper equipment is found it is often not designed to work together as a system.

In part because of this, CVC procedures are performed only by registered nurses or doctors, with the procedure consuming a large quantity of their valuable time. The patient and other care-givers are often forced to remain idle while waiting for the qualified persons to find time to provide the catheter access service.

As an additional complication, access to a CVC by needle gives rise to a potential source of injury and infection to the care-giver through contact with the needle. This is particularly important when the patient being treated has a dangerous infection, such as HIV or hepatitis. Often, the care-giver and patient are unaware that an infection is present.

In addition to CVC maintenance and operation as described above, it can be highly desirable in emergency situations to get a plurality of medications quickly into a patient's bloodstream through a CVC or other catheter. It would be highly desirable in such situations for the care-giver to have a catheter access system which facilitates multiple accesses to the catheter.

Our U.S. Patent No. 5,308,322, formerly U.S. patent application Ser. No. 08/048,906, and our U.S. Pat. No. 5,411,485, formerly U.S. patent application Ser. No. 08/187,632, are hereby incorporated by reference.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts." U.S. Constitution, Article 1, Section 8.

In accordance with one aspect of the invention, a catheter access system comprises:

an integrally molded first sheet forming a plurality of syringe channels, the syringe channels projecting outwardly from the first sheet and having longitudinal lengths formed along the first sheet;

a second sheet laminated to the first sheet, the second sheet extending along the syringe channels to enclose the syringe channels along their longitudinal lengths, the enclosed syringe channels defining a plurality of syringe barrels;

an independently operable syringe plunger slidably received within each syringe barrel;

a syringe barrel selection valve associated within the laminated first and second sheets, the syringe barrel selection valve having a plurality of individually-selectable valve inlets, the syringe barrel selection valve having a valve outlet for fluid connection to a catheter access line in a patient; and the laminated first and second sheets defining individual fluid passages connecting individual syringe barrels to corresponding individual valve inlets.

In accordance with another aspect of the invention, a catheter access system comprises:

an integrally molded upper sheet forming a plurality of generally rectangular syringe channels, the syringe channels having longitudinal lengths formed along the upper sheet, each syringe channel having a top wall and a pair of side walls;

a lower sheet laminated to the upper sheet, the lower sheet being planar and extending along the syringe channels to form bottom walls along the syringe channels; the top, bottom, and side walls defining a plurality of syringe barrels which extend from rearward ends to forward ends along the laminated upper and lower sheets;

an independently operable syringe plunger slidably received within each syringe barrel;

the upper sheet being molded to form a valve housing projecting from the upper sheet, the valve housing having individual valve inlets corresponding to individual syringe barrels, the valve housing having a valve outlet for fluid connection to a catheter access line in a patient;

individual fluid passages formed between the upper and lower sheets, the individual fluid passages connecting individual syringe barrels to corresponding individual valve inlets; and a valve body mounted for movement within the valve housing to provide fluid communication between a selectable one of the valve inlets and the valve outlet.

The invention furthermore includes preferred methodical steps of fabricating a catheter access system. Such steps are described below along with preferred physical embodiments of the invention.

Figure 1:
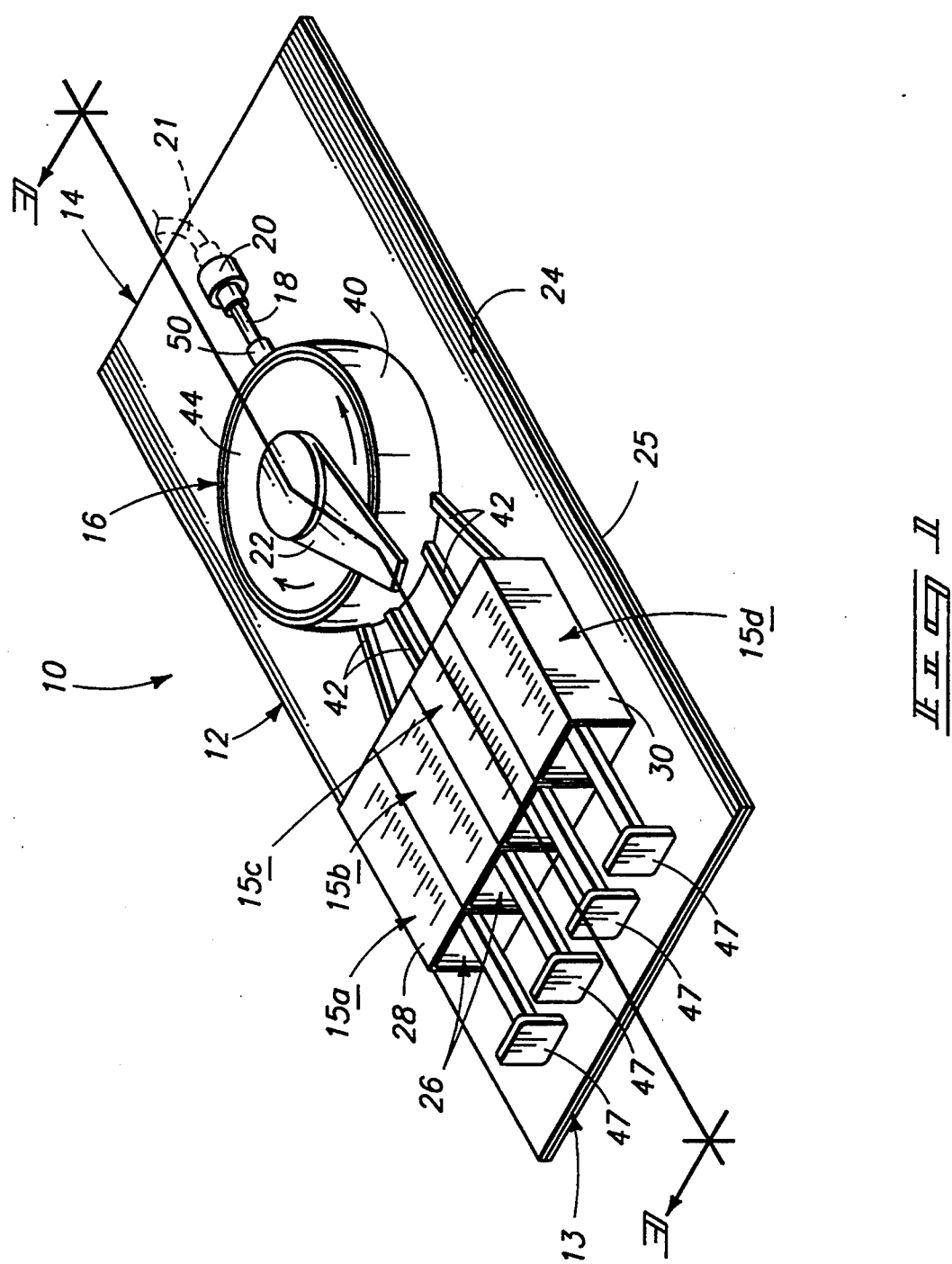
FIG. 1 is a top perspective view of a preferred embodiment catheter access system in accordance with the invention.
Figure 2:
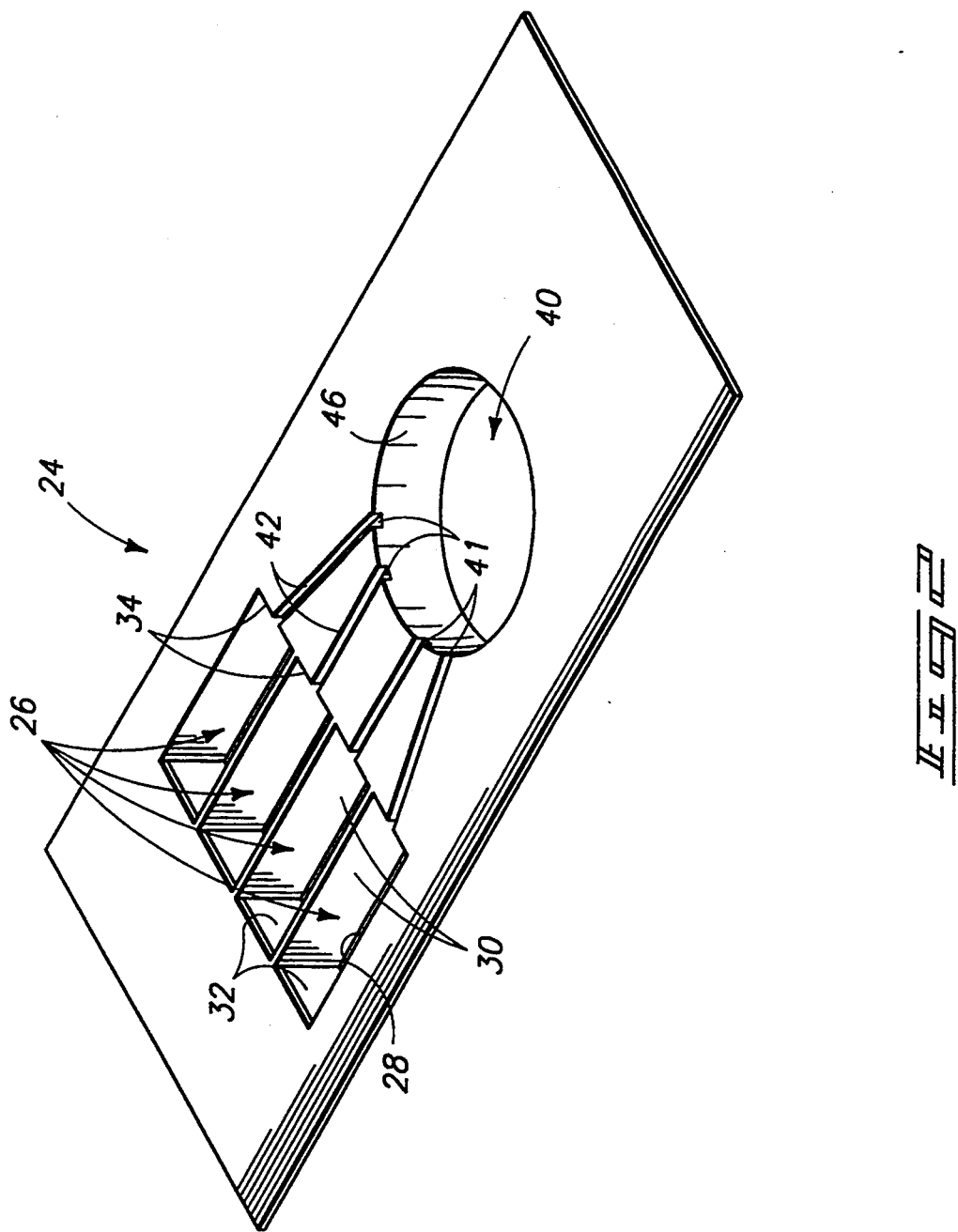
FIG. 2 is a bottom perspective view of an upper molded sheet which forms part of the catheter access system of FIG. 1.
Figure 3:
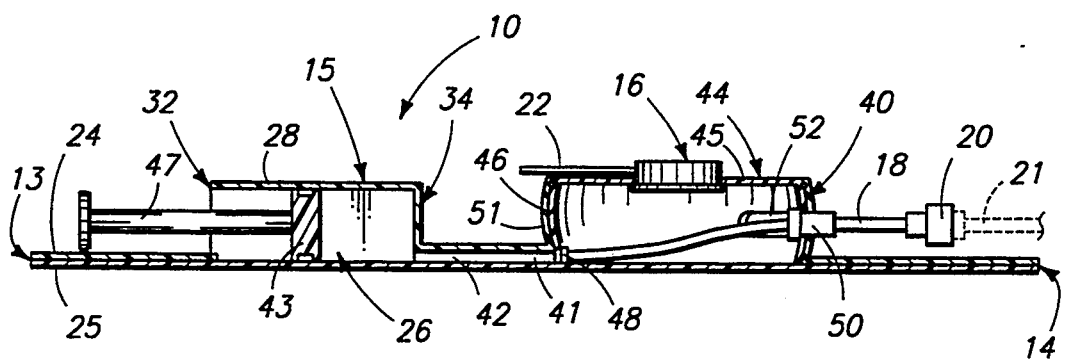
FIG. 3 is an offset partial sectional view taken generally along the line 3—3 of FIG. 1.

FIGS. 1–3 show a preferred embodiment of the invention, indicated generally by reference numeral 10. Catheter access system 10 includes a rectangular sterile supporting sheet or base 12 which extends in a longitudinal direction from a rearward end 13 to a forward end 14. Access system 10 also includes a plurality of syringe barrels 15a–15d (referred to collectively as syringe barrels 15) and a syringe barrel selection valve 16, each of which is attached integrally to sterile supporting sheet or base 12. Syringe barrels 15 have longitudinal axes which extend in the longitudinal direction of supporting base 12. Barrel selection valve 16 is positioned toward forward end 14 of supporting base 12 forwardly from syringe barrels 15.

A valve outlet or tube 18 extends from syringe barrel selection valve 16 toward base forward end 14. Valve outlet tube 18 has a Luer-lok connector 20 at its outer end to facilitate needle-less connection between access system 10 and a catheter access line 21, such as a central venous catheter in a patient. Syringe barrel selection valve 16 has a handle or knob 22 which can be positioned or turned by a care-giver to provide fluid communication between a selected one of syringe barrels 15 and valve outlet tube 18.

Supporting base 12 is formed by laminated first and second (upper and lower) sheets 24 and 25. Upper sheet 24 is shown by itself in FIG. 2. It is formed by integrally molding a plurality of generally rectangular syringe channels 26 in a thin sheet of medically-approved plastic such as high-density polypropylene, using common blow-molding or injection processes. The syringe channels project upwardly or outwardly from upper sheet 24, having rectangular transverse cross sections and longitudinal lengths which are formed longitudinally along upper sheet 24. The channels are open toward the bottom or under side of upper sheet 24. Each channel has a top wall 28 and pair of longitudinally-extending sidewalls 30. The channels are formed to adjoin each other in side-by-side and parallel relationship. They extend from rearward ends 32 to forward ends 34. After molding, rearward ends 32 are opened by cutting them away for plunger insertion. Forward ends 34 remain closed, but for fluid passages which are described below.

Syringe barrel selection valve 16 comprises a generally cylindrical valve housing 40 formed by molding upper sheet 24. Cylindrical valve housing 40 projects upwardly or outwardly from upper sheet 24. It is formed by an excurved or outwardly convex circumferential sidewall 51. In addition, a plurality of individual fluid passages 42 are molded generally longitudinally along upper sheet 24. Each fluid passage extends between an individual syringe channel 26 and valve housing 40. In the preferred embodiment, valve housing 40 is molded to have an upper portion (not shown) which is cut out after molding. Also in the preferred embodiment, fluid passages 42 are molded as open furrows or grooves along upper sheet 24.

Lower sheet 25 is preferably a planar sheet of plastic, such as medically-approved high-density polypropylene. Access system 10 is formed by laminating planar lower sheet 25 beneath upper sheet 24 in a manner which extends lower sheet 25 along channels 26, fluid passages 42, and valve housing 40. Lower sheet 25 thus encloses syringe channels 26 along their longitudinal lengths and defines syringe barrels 15. Laminating lower sheet 25 to upper sheet 24 also closes fluid passages 42 along their lengths, and similarly closes the lower portion of valve housing 40. More specifically, lower sheet 25 forms lower walls along channels 26, along fluid passages 42, and beneath valve housing 40. Syringe barrels 15 are defined and enclosed by top walls 28, side walls 30, and by the lower walls formed by lower sheet 25.

An independently operable syringe plunger 43 is thereafter slidably received within each syringe barrel. Each syringe plunger 43 is preferably rectangular to fit snugly and sealingly within its syringe barrel. An elongated handle 47 extends from each plunger 43, through open rearward end 32 of the corresponding syringe channel 26.

Valve housing 40 includes a plurality of individually-selectable valve inlets 41. Each valve inlet 41 is formed by the intersection of one of fluid passages 42 with valve housing 40, and corresponds to an individual syringe barrel. Individual fluid passages 42 therefore connect individual syringe barrels 15 to corresponding individual valve inlets 41 of valve housing 40.

A rotatable valve body 44 is mounted and retained within valve housing 40 for rotatable, fluid sealing movement therein. Valve body 44 comprises a hollow plastic cylindrical drum which is downwardly open, having a flat top surface 45 and an excurved or outwardly convex circumferential sidewall 46. The outer shape and size of valve body 44 is complementary to the inner shape and size of valve housing sidewall 51 for a close but sliding fit. The convex or bowed surfaces mate with each other to retain valve body 44 within valve housing 40, while being flexible enough to permit convenient assembly of the rotatable vale assembly.

Handle 22 is affixed to top surface 45. Outlet tube 18 extends from a first end 48, within valve body 44, to a second end at connector 20. Tube 18 extends through the forward end of valve housing 40, being secured to valve housing 40 by a grommet or sonic weld 50. Valve body 44 has a slot 52 to accommodate rotational movement of valve body 44 relative to outlet tube 18 and grommet 50. First end 48 of outlet tube 18 is connected to and communicates through cylindrical sidewall 46 of valve body 44. Rotation of valve body 44 aligns first end 48 with a selected one of valve inlets 41 to provide fluid communication between said selected one of the valve inlets and valve outlet tube 18. Outlet tube 18 is flexible so that it does not restrict free rotational movement of valve body 44 relative to valve housing 40.

While the valve body described is believed to be preferable, it might alternatively be desirable to fabricate valve body 44 as a solid cylindrical element with one or more apertures or channels formed therethrough to communicate between outlet tube 18 and a selected one of valve inlets 41. In this case, tube 18 would terminate at the forward end of sidewall 46 rather than extending into valve housing 40.

The construction and fabrication methods described above should be inexpensive to implement. Most of the components are formed by the laminated sheets. For instance, the syringe barrels, the valve housing, and the individual fluid passages are all defined by and between the upper and lower sheets. It is possible to define these components by molding them into either or both of the sheets. However, it is preferable to utilize a planar lower sheet and to mold all desired features into the upper sheet. In addition to being less expensive, this provides a planar base which can be conveniently taped to a patient or clipped to a patient's gown during catheter access operations. Furthermore, at least one of the laminated upper and lower sheets which forms support base 12 preferably has a longitudinal extent or dimension which is greater than a combined longitudinal extent of the syringe barrels and the valve housing. When the access system is packaged in a sterile condition, base 12 provides a sterile field underlying the access components to facilitate sterile connection procedures. Taping the base to a patient greatly simplifies the task of maintaining the cleanliness and sterility of components during catheter access.

The above-described catheter access system 10 can be used either to inject medication or other solutions into patients through a CVC or other catheter, or to withdraw a patient's blood through the catheter. In either case, the sequence of steps required to accomplish the desired fluid transfers to or from the patient can be accomplished without the numerous and sequential independent connections previously required. As an example, steps involved in administering a patient medication where heparin removal is first required are described below. Catheter access system 10 is preferably provided in a pre-filled condition by or for the caregiver, ready for immediate connection to a CVC access lumen in a patient, for example. By way of example only, a first syringe barrel 15a would not be pre-filled, but would instead be utilized as a fluid withdrawal syringe. A second syringe barrel 15b would be pre-filled with a desired medication. Alternatively, second syringe 15b could be a non-integral syringe which would be filled and connected to access system 10 during or just before use. A third syringe barrel 15c would be pre-filled with a flushing saline, and a fourth syringe barrel 15d would be pre-filled with heparin prior to any access to the catheter. Also, the internal volume of the various fluid conduits and passageways of the system, such as outlet tube 18 and fluid passages 42, would preferably be initially pre-filled with saline to eliminate air.

With connector 20 of the system connected with the patient's catheter, handle 22 is turned to select the first syringe barrel 15a by aligning first end 48 of outlet tube 18 with the fluid passage 42 leading to first syringe barrel 15a. The plunger 43 of syringe barrel 15a is then withdrawn to withdraw heparin-containing blood from the patient's catheter. Handle 22 is then turned to select second syringe barrel 15b. Medication from syringe barrel 15b is pushed into the catheter and patient. Handle 22 is turned again to select third syringe barrel 15c. Saline is then pushed in to clear all medication from the catheter into the patient, leaving saline in the catheter. Handle 22 is turned one more time to select fourth syringe barrel 15d, and the plunger of syringe barrel 15d is depressed to establish a heparin lock within the patient's catheter.

Appropriate indicia are preferably provided on or adjacent barrel selection valve 16 to indicate proper handle positions and to prompt the care-giver to carry out the administration steps in the correct sequence. Valve positions are preferably arranged so that turning handle 22 in one direction to sequential positions will facilitate the desired order of steps.

The above system could, of course, be utilized in other manners for administering one or more medications to a patient's catheter or for withdrawing blood for analysis from a catheter, as will be appreciated by medical personnel of skill in the art. By way of example only, the above system could be utilized in emergency situations where a typical sequence of multiple drugs might need to be administered through a patient's catheter apart from any association with a catheter having a heparin lock. In such instances, many or all of the barrels of the syringe apparatus might be provided with medication, as opposed to saline.

Figure 4:
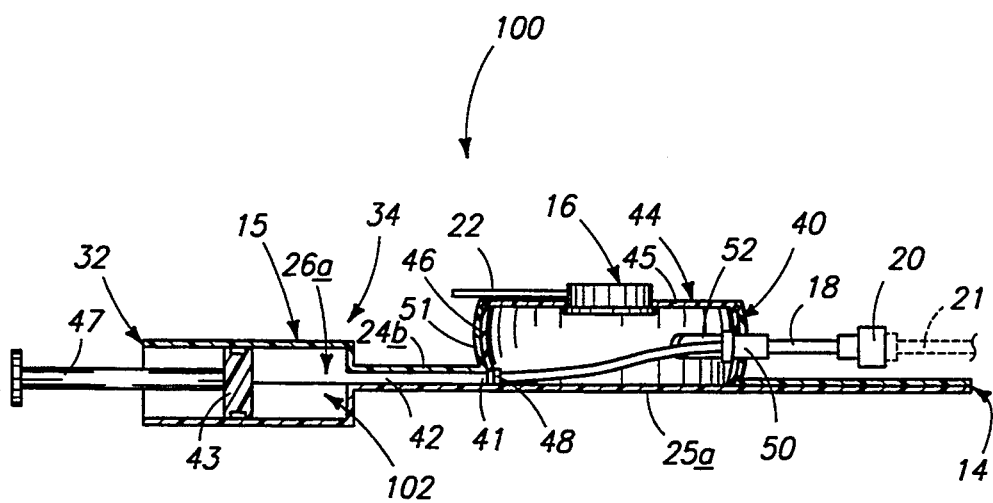
FIG. 4 is a sectional view, similar to that of FIG. 3, showing an alternative embodiment of the invention.

FIG. 4 shows an alternative construction catheter access system 100. Access system 100 is largely similar to access system 10 of the above first-described embodiment. Accordingly, identical reference numbers have been used in FIG. 4 where appropriate. The access system of FIG. 4 differs from that of FIGS. 1-3 primarily in the formation of syringe barrels 15. Specifically, lower sheet 25a is integrally molded to form a plurality of lower syringe channels 102 in lower sheet 25a opposite corresponding syringe channels 26a of upper sheet 24a. Corresponding syringe channels 102 and 26a are positioned in juxtaposition to each other to define syringe barrels 15 in combination with each other.

Figure 5:
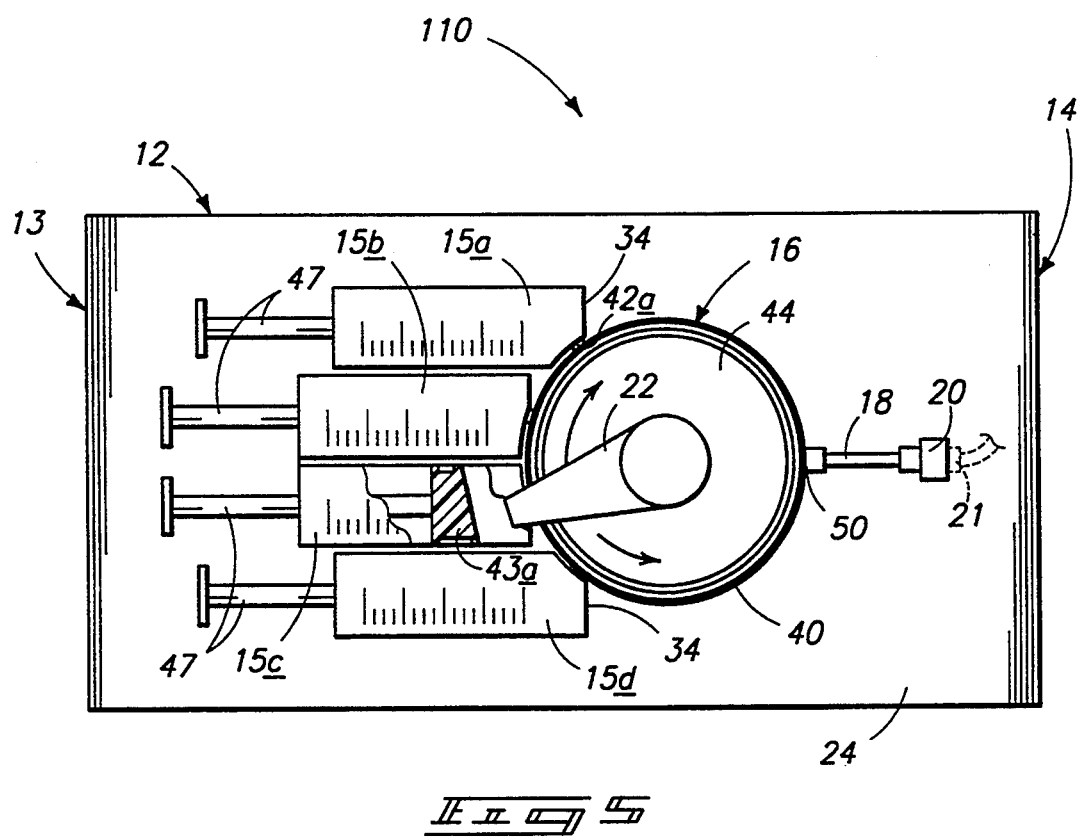
FIG. 5 is a top view of another alternative embodiment of the invention.
Figure 6:
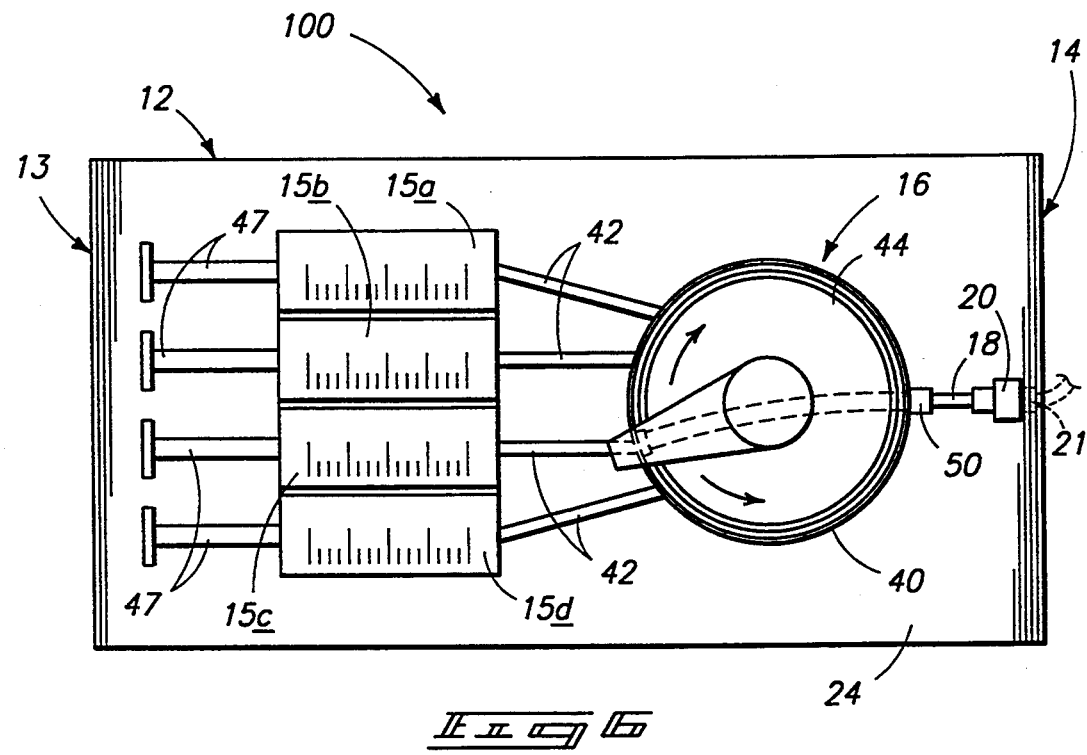
FIG. 6 is a top view of the embodiment of FIG. 5 showing the cross-section of the connecting valve.

FIGS. 5 and 6 show another alternate embodiment catheter access system in accordance with the invention, generally referenced by the numeral 110. Access system 110 is similar in construction to the above-described preferred embodiment of FIGS. 1-3, such that only differences will be described. The primary difference in the access system of FIG. 5 is in the longitudinal positions of syringe barrels 15. Specifically, forward ends 34 of the side-by-side syringe barrels are longitudinally staggered to abut or be in juxtaposition to cylindrical valve housing 40. This reduces the length of fluid passages 42a and therefore reduces the "dead" or non-expelled volume associated with each syringe. In order to further reduce such dead volume, plungers 43a are beveled or otherwise contoured to match the general angle or shape of forward ends 34 of the corresponding syringe barrels.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A catheter access system comprising:
   an integrally molded first sheet forming a plurality of syringe channels, the syringe channels projecting outwardly from the first sheet and having longitudinal lengths formed along the first sheet;
   a second sheet laminated to the first sheet, the second sheet extending along the syringe channels to enclose the syringe channels along their longitudinal lengths, the enclosed syringe channels defining a plurality of syringe barrels;
   an independently operable syringe plunger slidably received within each syringe barrel;
   a syringe barrel selection valve associated within the laminated first and second sheets, the syringe barrel selection valve having a plurality of individually-selectable valve inlets, the syringe barrel selection valve having a valve outlet for fluid connection to a catheter access line in a patient; and
   the laminated first and second sheets defining individual fluid passages connecting individual syringe barrels to corresponding individual valve inlets.

2. The catheter access system of claim 1 wherein the individual fluid passages are formed between the laminated first and second sheets.

3. The catheter access system of claim 1 wherein the individual fluid passages are formed by furrows in at least one of the first and second sheets.

4. The catheter access system of claim 1 wherein at least one of the laminated first and second sheets has a longitudinal extent which is greater than a combined longitudinal extent of the syringe barrels and the syringe selection valve.

5. The catheter access system of claim 1 wherein the second sheet is planar, the individual fluid passages being formed by furrows in the first sheet.

6. The catheter access system of claim 1, the second sheet being integrally molded to form a plurality of syringe channels in the second sheet opposite corresponding syringe channels of the first sheet, corresponding syringe channels of the first and second sheets defining the plurality of syringe barrels.

7. The catheter access system of claim 1 wherein the syringe channels have rectangular cross-sections.

8. The catheter access system of claim 1, the syringe barrels adjoining each other in parallel and side-by-side relationship.

9. The catheter access system of claim 1, the syringe barrel selection valve including a generally cylindrical valve housing projecting from the first sheet, the syringe barrels adjoining each other in parallel and side-by-side relationship, the side-by-side syringe barrels having forward ends which are longitudinally staggered in juxtaposition to the cylindrical valve housing.

10. The catheter access system of claim 1, the syringe barrel selection valve comprising:
    a generally cylindrical valve housing formed between the first and second sheets;
    a valve body within the cylindrical valve housing, the valve body being rotatable to provide fluid communication between a selectable one of the valve inlets and the valve outlet.

11. The catheter access system of claim 1, the syringe barrel selection valve comprising:

a generally cylindrical valve housing formed between the first and second sheets, the valve housing having an excurved circumferential sidewall;

a valve body within the cylindrical valve housing, the valve body having an excurved circumferential sidewall which is complementary in size and shape to the valve housing sidewall, the valve body being rotatable to provide fluid communication between a selectable one of the valve inlets and the valve outlet.

12. The catheter access system of claim 1 and further comprising a flexible outlet tube, the syringe barrel selection valve comprising a rotatable valve body positioned within the laminated first and second sheets, the flexible outlet tube having a first end which is connected to the valve body to be aligned by rotation of the valve body with a selected one of the valve inlets, the flexible outlet tube having a second end for connection to the catheter access line.

13. A catheter access system comprising:
an integrally molded upper sheet forming a plurality of generally rectangular syringe channels, the syringe channels having longitudinal lengths formed along the upper sheet, each syringe channel having a top wall and a pair of side walls;
a lower sheet laminated to the upper sheet, the lower sheet being planar and extending along the syringe channels to form bottom walls along the syringe channels; the top, bottom, and side walls defining a plurality of syringe barrels which extend from rearward ends to forward ends along the laminated upper and lower sheets;
an independently operable syringe plunger slidably received within each syringe barrel;
the upper sheet being molded to form a valve housing projecting from the upper sheet, the valve housing having individual valve inlets corresponding to individual syringe barrels, the valve housing having a valve outlet for fluid connection to a catheter access line in a patient;
individual fluid passages formed between the upper and lower sheets, the individual fluid passages connecting individual syringe barrels to corresponding individual valve inlets; and
a valve body mounted for movement within the valve housing to provide fluid communication between a selectable one of the valve inlets and the valve outlet.

14. The catheter access system of claim 13 wherein the individual fluid passages are formed by furrows in the upper sheet.

15. The catheter access system of claim 13 wherein at least one of the laminated upper and lower sheets has a longitudinal extent which is greater than a combined longitudinal extent of the syringe barrels and the valve housing.

16. The catheter access system of claim 13, the syringe barrels adjoining each other in parallel and side-by-side relationship.

17. The catheter access system of claim 13 wherein the valve housing is generally cylindrical, the valve body being rotatable within the cylindrical valve housing.

18. The catheter access system of claim 13 wherein the valve housing has an excurved circumferential sidewall, the valve body having a mating excurved circumferential sidewall, the valve body being rotatable within the cylindrical valve housing.

19. The catheter access system of claim 13, the valve housing being generally cylindrical, the syringe barrels adjoining each other in parallel and side-by-side relationship, the forward ends of the side-by-side syringe barrels being longitudinally staggered in juxtaposition to the cylindrical valve housing.

20. The catheter access system of claim 13 and further comprising a flexible outlet tube, the valve body being rotatable within the valve housing, the flexible outlet tube having a first end which is connected to the valve body to be aligned by rotation of the valve body with a selected one of the valve inlets, the flexible outlet tube having a second end for connection to the catheter access line.

21. A method of fabricating a catheter access system comprising the following steps:
molding a plurality of syringe channels in a first sheet, the syringe channels projecting outwardly from the first sheet and having longitudinal lengths formed along the first sheet;
molding a valve housing in the first sheet;
molding a plurality of fluid passages along the first sheet, the fluid passages connecting individual syringe channels to the valve housing;
laminating a second sheet to the first sheet in a manner which extends the second sheet along the syringe channels to enclose the syringe channels along their longitudinal lengths, the enclosed syringe channels defining a plurality of syringe barrels;
positioning an independently operable syringe plunger for slidable movement within each syringe barrel;
positioning a valve body within the valve housing to provide fluid communication between a valve outlet and a selectable one of the fluid passages.

22. A method as recited in claim 21 wherein the step of molding the fluid passages comprises molding a plurality of furrows in the first sheet, the laminated second sheet enclosing the furrows to form the fluid passages.

23. A method as recited in claim 21 and further comprising molding a plurality of syringe channels in the second sheet opposite corresponding syringe channels of the first sheet, corresponding syringe channels of the first and second sheets defining the plurality of syringe barrels.

24. A method as recited in claim 21 wherein the step of molding the syringe channels comprises molding rectangular syringe channels.

* * * * *